(12) United States Patent
Choudary et al.

(10) Patent No.: US 6,455,735 B1
(45) Date of Patent: *Sep. 24, 2002

(54) PROCESS FOR THE PREPARATION OF AMINE OXIDES

(75) Inventors: Boyapati M. Choudary; Balagam Bharathi; Mannepalli L. Kantam; Chinta R. V. Reddy; Kondapuram V. Raghavan, all of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/963,785

(22) Filed: Sep. 27, 2001

Related U.S. Application Data

(63) Continuation-in-part of application No. 09/721,585, filed on Nov. 22, 2000, now Pat. No. 6,323,367.

(51) Int. Cl.[7] .................... C07C 291/04; C07D 217/22; C07D 211/30; C07D 265/30
(52) U.S. Cl. ................. 564/298; 546/141; 546/188; 546/189; 544/106; 544/107
(58) Field of Search ................... 564/297, 298; 546/141, 188, 189; 544/106, 107

(56) References Cited

U.S. PATENT DOCUMENTS

| 3,215,741 A | 11/1965 | Chadwick |
| 3,274,252 A | 9/1966 | Albert et al. |
| 3,283,007 A | 11/1966 | Chadwick |
| 3,424,780 A | 1/1969 | Sayigh |
| 4,565,891 A | 1/1986 | Correa et al. |
| 4,596,874 A | 6/1986 | Murahashi et al. |
| 4,774,212 A | 9/1988 | Drezdon |
| 4,889,954 A | 12/1989 | Laurenzo et al. |
| 5,130,488 A | 7/1992 | Smith et al. |
| 6,124,506 A | 9/2000 | Atkins et al. |

OTHER PUBLICATIONS

Zajac, Jr. et al, Oxidation of Amines with 2–Sulfonyloxaziridines (Davis' Reagents), J. Org. Chem., 1988, 53, 5856–5860.
Murray et al, "Synthesis of Nitrones Using the Methyltrioxorhenium/Hydrogen Peroxide System", J. Org. Chem., 1996, 61, 8099–8102.
Murahashi et al, "Tungstate–Catalyzed Oxidation of Secondary Amines to Nitrones, α–Substitution of Secondary Amines via Nitrones", J. Org. Chem., 1990, 55, 1736–1744.
Venkatachalapathy et al., "A Clean Clay Catalysed Synthesis of A, N–Diarylnitrones", SYNTHETIC COMMUNICATIONS, Marcel Dekker, Inc., Basel, CH, vol. 27, No. 23, 1997, pp. 4041–4047, XP000876142.

Primary Examiner—Johann Richter
Assistant Examiner—Sikarl A. Witherspoon
(74) Attorney, Agent, or Firm—Nixon & Vanderhye P.C.

(57) ABSTRACT

The present invention provides a process for the preparation of high quality amine oxide by reacting a tertiary or secondary amine with hydrogen peroxide as an oxidant in presence of a recyclable heterogeneous layered double hydroxide exchanged with one of the anions of transition metal oxides as a catalyst in a solvent selected from the group consisting of water, water containing dodecylbenzenesulfonic acid sodium salt as additive, and a water miscible organic solvent.

8 Claims, No Drawings

PROCESS FOR THE PREPARATION OF AMINE OXIDES

This application is a continuation-in-part of application Ser. No. 09/721,585, filed Nov. 22, 2000, now U.S. Pat. No. 6,323,367, the entire content of which is hereby incorporated by reference in this application.

FIELD OF THE INVENTION

The present invention relates to an improved process for the preparation of high quality amine oxides from secondary and tertiary aliphatic amines. More particularly, the present invention relates to an improved process for the preparation of amine oxides from secondary and tertiary aliphatic amines useful in the preparation of hair conditioners and shampoos, toothpaste, laundry detergent powder, fabric softeners, toilet soap bars and cosmetics, surfactants as well as in other applications as synthetic intermediates and excellent spin trapping reagents.

BACKGROUND OF THE INVENTION

The N-oxides holds a key position in the chemistry of heterocycles as well as in biomedical area. The tertiary amine oxides are widely used in treatment of fabrics and preparation of hair conditioners and shampoos, toothpaste, laundry detergent powder, fabric softeners, toilet soap bars and cosmetics as well as in other applications. They were also used as stoichiometric oxidants in metal catalysed hydroxylation and epoxidation reactions of olefins. On the other hand, the oxides derived from secondary amines, called nitrones are highly valuable synthetic intermediates and excellent spin trapping reagents. In particular nitrones are excellent 1,3 dipoles and have been utilized for the synthesis of various nitrogen containing biologically active compounds e.g. alkaloids and lactams.

Conventionally tertiary amine oxides are prepared by oxidation of respective tertiary amines with strong oxidising agent like aqueous hydrogen peroxide in a solvent such as water, lower alcohol, acetone or acetic acid. A dilute or preferably concentrated (30–90% by weight) hydrogen peroxide solution is added in stoichiometric or greater amount to an aqueous solution containing the tertiary amine to obtain amine oxide, (U.S. Pat. NO. 3,215,741). The drawback is that the reaction transforms into a gel resembling a thick paste long before completion of the reaction, which retards further reaction. The yields are only 30–40% by weight of amine oxide. Later several methods such as incorporation of catalyst and/chelating agent have been developed to in order to increase the quality and yields of the product.

In case of secondary amines, the classical methods involve the condensation of N-monosubstituted hydroxylamines with carbonyl compounds or the direct oxidation of N,N-disubstituted hydroxylamines. Later direct oxidation of secondary amines using several oxidising systems such as $R_2C(\mu-O_2)$, $Na_2WO_4$—$H_2O_2$, $SeO_2$, TPAP-NMO land UHP-M (M=Mo, W), MTO—$H_2O_2$ have been developed to accomplish nitrones under homogeneous conditions. The drawback in all the above cases is the difficulty in recovering the homogeneous catalyst/reagents from the reaction mixture.

Reference may be made to a U.S. Pat. No. 3,283,007 wherein the oxidation of tertiary amines using diethelene triamine penta/tetra acetic acid as chelating agent and sometimes contaminated with heavy metals is recommended to improve the yield. The hydrogen peroxide solution employed has concentration of at least 30–75% by weight. The disadvantages of this process are high reaction temperatures ranging between 40–100° C., longer reaction periods, and lower yields of amine oxides.

Reference may be made to U.S. Pat. No. 3,424,780, wherein high yields of tertiary amine oxides are achieved by carrying the oxidation of tertiary amine with 30–70% by weight of aqueous hydrogen peroxide using 0.01 to 2% weight of carbondioxide, in presence of a chelating agent, tetra acetylene diamine, a salt thereof, polyphosphates, stannates, a hydroxy carboxylic acid salts or the salt of poly carboxylic acid. The reaction is carried out at a temperature ranging from 40 to 80° C. The disadvantages of this process are high reaction temperature, longer reaction periods and the amine oxide formed is intensively coloured when carbon dioxide atmosphere is used to speed up the reaction and this method necessitates injecting a gas which requires handling facilities. Another disadvantage is more than 30% by weight of hydrogen peroxide is not environmentally friendly.

Reference may be made to another U.S. Pat. No. 4,889,954 wherein the tertiary amines are reacted in high yields to give the corresponding amine oxides with a low content of nitrosamine, the oxidation of tertiary amine being carried out in the presence of a dialkyl carboxylic acid ester as catalyst and if appropriate, ascorbic acid as a co-catalyst using 45–70% by weight of hydrogen peroxide. The drawbacks in the above process are the requirement of frequent addition of water to avoid gel formation, high reaction temperatures, longer reaction periods and difficulty in separation of the catalyst from the reaction mixture.

Reference may be made to another U.S. Pat. No. 4,565,891 wherein octacyano molybdate or iron salts are used as catalysts and molecular oxygen for oxidation of tertiary amines at high pressures and temperatures. The main drawback of this process is the need of very high temperature of 90–130° C. and very low yields of amine oxide reporting 11–52% of conversion.

Reference may be made to a U.S. Pat. No. 5,130,488 wherein the solid amine oxide can be prepared by reacting a tertiary amine with hydrogen peroxide using carbon dioxide in presence of acetate and cooling to precipitate the product. This process is superior to previously known methods of preparing amine oxides. However, its use can sometimes lead to cleavage of the solvents, plating on the walls of the vessel used for the precipitation, contamination of the product with residual peroxide, and or discoloration of the product.

Reference may be made to a publication by Walter W. Zajac et al., J. Org. Chem.; 53, 5856, 1988 wherein the oxidation of secondary and tertiary amines using 2-sulfonyloxyxaziridines (Davis Reagents) were reported. The drawback of the above process is, the reagent was used in stoichiometric amounts.

Reference may be made to a publication by Shun-Ichi Murahashi et al., J. Org. Chem.; 55, 1736, 1990 wherein the sodium tungstate was used as catalyst for the oxidation of secondary amines. The drawback is the difficulty in recovery of the catalyst from homogeneous conditions.

Another reference may be made to publication by Murraay et al., J. Org. Chem.; 61, 8099, 1996 wherein methyltrioxorhenium was used as a catalyst in oxidation of secondary amines. The drawback is the difficulty in recovery of the catalyst.

OBJECTS OF THE INVENTION

The main object of the present invention is to provide an eco-friendly and simple process for N-oxidation of secondary and tertiary amines using layered double hydroxides exchanged with anions of transition metal oxides as a catalyst, which is cheaper, non-corrosive and recyclable catalyst utilising only lower percentage of hydrogen peroxide at room temperatures to give high yields of product.

Another object of the present invention is to provide an improved process for the preparation of tertiary amine oxides and secondary amine oxides (nitrones), widely used in detergents, shampoos, fabric softers and biomedical area.

Another object of the present invention is the use of non-corrosive and low cost heterogeneous catalyst i.e. layered double hydroxides exchanged with tungstate, molybdate, vanadate and their polyanions.

A further object of the invention is to provide a environmentally friendly process for the preparation of tertiary amine oxides and nitrones, using water alone or in combination with dodecylbenzenesulfonic acid sodium salt as an additive.

SUMMARY OF THE INVENTION

Accordingly, the present invention provides an improved process for the preparation of amine oxides of a very high quality which comprises reacting tertiary and secondary amines with hydrogen peroxide as an oxidant in presence of a recyclable heterogeneous catalyst, layered double hydroxides exchanged with anion of transition metal oxides, with tungstate, molybdate, vanadate, and their polyanions i.e. polyoxometallates, in a solvent selected from water, water containing dodecylbenzzenesulfonic salt additive or a water miscible organic solvent at a temperature ranges between 10–25° C. for a period of 1–6 hours under continuous stirring and separating the product by simple filtration and subsequently evaporation of solvents by known methods.

IN an embodiment of the present invention, the heterogeneous catalyst used is the layered double hydroxides exchanged with transition metal oxides selected from a group consisting of tungstate, molybdate, vanadate and their polyanions i.e. polyoxometalates. Having formula I: $[M^{II}_{(1-x)}M^{III}_x(OH)_2][M^{n-}]_{x/2}.zH_2O$, which is derived from LDH having formula II $[M^{II}_{(1-x)}M^{III}_x(OH)_2][A^{n-}]_{x/2}.zH_2O$ where M is a transition metal oxides selected from the group consisting of W, Mo, V and $A^{n-}$ is interstitial anion, selected from nitrate, chloride and $M^{II}$ is a divalent cation selection from the group consisting of $Mg^{2+}$, $Mn^{2+}$, $Fe^{2+}$, $V^{2+}$, $Co^{2+}$, $Ni^{2+}$, $Cu^{2+}$, $Zn^{2+}$ $Pd^{2+}$, or $Ca^{2+}$ and $M^{III}$ is a trivalent ion selected from the group consisting of $Al^{3+}$, $Cr^{3+}$, $V^{3+}$, $Mn^{3+}$, $Fe^{3+}$, $Co^{3+}$, $Ni^{3+}$, $Rh^{3+}$, $Ru^{3+}$, $Ga^{3+}$ or $La^{3+}$.

In another embodiment of the present invention, the tertiary amines used are having the general formula $R^1R^2NR^3$ wherein $R^1$, $R^2$ and $R^3$, which may be the same or different, and are the straight-chain or branched-chain groups selected from alkyl, alkenyl and aralkyls having $C_1$–$C_{24}$ carbons selected from N,N-dimethyl decyl amine, N,N-dimethyl dodecyl amine, N,N-dimethylbenzylamine, triethylamine, tributylamine and cyclic amines selected from imidazolines pyridines, N-substituted piperazines, N-substituted piperadines or N-substituted morpholines, e.g., N-methylmorpholine.

In another embodiment of the present invention, the secondary amines used are having general formula $R^1R^2NH$ wherein $R^1$ and $R^2$ may be the same or different and are the straight-chain or branched-chain groups selected from alkyl, alkenyl and aralkyls having $C_1$–$C_{24}$ carbons, selected from dibutyl amine, dibenzyl amine, N-benzyl phenethylamine, N-phenyl benzylamine and cyclic amines selected from piperidine, 1,2,3,4, tetrahydro isoquinoline.

In another embodiment of the present invention aqueous hydrogen peroxide is added slowly in a controlled manner for a period ranges between 0–120 min.

In yet another embodiment of the present invention, the catalyst introduced in the system is 6–12% by weight of anion of transition metal oxides selected from tungstate, molybdate, vanadate and their polyanions as polyoxometalates.

In still another embodiment of the present invention, water miscible organic solvents selected from group consisting of methonol, ethanol, isopropanol, 1-propanol, 1-butanol, 2-butanol and isobutyl alcohol are used.

In still another embodiment of the present invention, the amount of hydrogen peroxide used is 2 to 6 moles per mole of amine.

DETAILED DESCRIPTION OF THE INVENTION

The catalyst of the invention comprises a recyclable heterogeneous catalyst, i.e. layered double hydroxides exchanged with tungstate, molybdate, vanadate and their polyanions i.e. polyoxometalates that catalyses oxidation of secondary and tertiary amines in a water miscible organic solvent, water or in water with dodecylbenzenesulfonic acid sodium salt as an additive. The advantages such as low cost of the catalyst, reusability for several times and its ability to oxidise the amines at 10–25° C., below or at room temperature in a shorter period make the present invention as a promising candidate for a clean and efficient industrial route to amine oxide preparation.

Parent/Copending Application No. 09/721,585 discloses a process for the process for the preparation of amine oxides of high quality by reacting tertiary and secondary amines with hydrogen peroxide as an oxidant in presence of a recyclable heterogeneous catalyst, layered double hydroxides exchanged with anion of transition metal oxides, with tungstate, molybdate, vanadate, and their polyanions i.e. polyoxometallates, in a water miscible organic solvent at a temperature ranges between 10–25° C. for a period of 1–6 hours under continuous stirring and separating the product by simple filtration and subsequently evaporation of solvents by known methods.

The novelty of the present invention lies in the use of heterogeneous catalyst for the first time for the N-oxidation of secondary and tertiary amines. The anion of transition metal oxides intercalated in the layered double hydroxide effectively catalyses the oxidation of amines to amine oxides. The catalyst was removed by simple filtration and the solid catalyst obtained thus is recycled for several times without any addition of fresh catalyst. The consistent activity for several cycles, mild reaction conditions, shorter reaction times makes the process economical and possible for commercial realisation.

According to the invention, amine oxides of a very high quality are prepared by reacting tertiary and secondary amines with hydrogen peroxide as an oxidant in presence of a recyclable heterogeneous catalyst, layered double hydroxides exchanged with anion of transition metal oxides, with tungstate, molybdate, vanadate, and their polyanions i.e. polyoxometallates, in an organic solvent at a temperature ranges between 10–25° C. for a period of 1–6 hours under continuous stirring and separating the product by simple filtration and subsequently evaporation of solvents by known methods.

The heterogeneous catalyst used is the layered double hydroxides exchanged with transition metal oxides selected from a group consisting of tungstate, molybdate, vanadate and their polyanions i.e. polyoxometalates. Having formula I: $[M^{II}_{(1-x)}M^{III}_x(OH)_2][M^{n-}]_{x/2}\cdot zH_2O$, which is derived from LDH having formula II $[M^{II}_{(1-x)}M^{III}_x(OH)_2][A^{n-}]_{x/2}\cdot zH_2O$ where M is a transition metal oxides selected from the group consisting of W, Mo, V and $A^{n-}$ is interstitial anion, selected from nitrate, chloride and $M^{II}$ is a divalent cation selected from the group consisting of $Mg^{2+}$, $Mn^{2+}$, $Fe^{2+}$, $V^{2+}$, $Co^{2+}$, $Ni^{2+}$, $Cu^{2+}$, $Zn^{2+}$ $Pd^{2+}$, or $Ca^{2+}$ and $M^{III}$ is a trivalent ion selected from the group consisting of $Al^{3+}$, $Cr^{3+}$, $V^{3+}$, $Mn^{3+}$, $Fe^{3+}$, $Co^{3+}$, $Ni^{3+}$, $Rh^{3+}$, $Ru^{3+}$, $Ga^{3+}$ or $La^{3+}$.

The tertiary amines used have the general formula $R^1R^2NR^3$ wherein $R^1$, $R^2$ and $R^3$, which may be the same or different, and are the straight-chain or branched-chain groups selected from alkyl, alkenyl and aralkyls having $C_1$–$C_{24}$ carbons selected from N,N-dimethyl decyl amine, N,N-dimethyl dodecyl amine, N,N-dimethylbenzylamine, triethylamine, tributylamine and cyclic amines selected from imidazolines pyridines, N-substituted piperazines, N-substituted piperadines or N-substituted morpholines, e.g., N-methylmorpholine. The secondary amines used have general formula $R^1R^2NH$ wherein $R^1$ and $R^2$ may be the same or different and are the straight-chain or branched-chain groups selected from alkyl, alkenyl and aralkyls having $C_1$–$C_{24}$ carbons, selected from dibutyl amine, dibenzyl amine, N-benzyl phenethylamine, N-phenyl benzylamine and cyclic amines selected from piperidine, 1,2,3,4, tetrahydro isoquinoline.

Aqueous hydrogen peroxide is added slowly in a controlled manner for a period ranges between 0–120 min. The catalyst introduced in the system is 6–12% by weight of anion of transition metal oxides selected from tungstate, molybdate, vanadate and their polyanions as polyoxometalates. The water miscible organic solvents are selected from group consisting of methanol, ethanol, isopropanol, 1-propanol, 1-butanol, 2-butanol and isobutyl alcohol are used. The amount of hydrogen peroxide used is 2 to 6 moles per moles of amine.

Scientific explanation:

The catalytic cycle in the oxidation of amines to amine oxides involves the easy formation of peroxotungstate, $HOOWO_3^-/HOOWO_6^-$ on interaction of tungstate with hydrogen peroxide. These peroxy species will act as an active species for the oxidation of secondary/tertiary amines as described by Murahashi et.al., for the $Na_2WO_4$ catalysed oxidation of secondary amines by hydrogen peroxide. The secondary amine undergoes nucleophilic reaction with peroxotungstate species to give hydroxylamine. Further oxidation of hydroxylamine followed by dehydration gives nitrone. In case of tertiary amines, the oxygen transfer occurs from peroxotungstate species to tertiary amine in a single step to form tertiary amine oxide. The species $HOWO_3^-/HOWO_6^-$ thus formed is readily oxidized with another molecule of $H_2O_2$ to give peroxo tungstate $HOOWO_3^-/HOOWO_6^-$, thus completing the catalytic cycle.

The following examples are given by way of illustration of the present invention and therefore should not be construed to limit the scope of the present invention.

EXAMPLE 1

Preparation of the various catalysts

1. Preparation of Mg—Al hydrotalcite (LDH) chloride:

Mg—Al—Cl hydrotalcite (3:1) is prepared as follows: About 200 ml of decarbonated and deionised water was taken into a 1 litre four necked round bottomed flask and stirred at 25° C. with a magnetic stirrer under a nitrogen flow. The mixture ($Al^{3+}$=0.05 mol/l), ($Mg^{2+}$=0.15 mol/l) of decarbonated solution of $AlCl_3 \cdot 9H_2O$ (12.07 g), $MgCl_2 \cdot 6H_2O$ (30.49 g) (obtained from M/s. Fluke, a Sigma Aldrich Company, Switzerland) and aqueous solution of sodium hydroxide (16 g, 0.2 mol/l) were added continuously drop-wise from a burette, the pH of the reaction mixture being kept at 10.00–10.2 during the reaction. The precipitate obtained was filtered, washed with deionised and decarbonated water and dried at 70° C. for 15 h.

a) Preparation of Mg—Al hydrotalcite (LDH) tungstate (Catalyst A):

To reach anion exchange of degree of 12%, 1 g of Mg—Al—Cl hydrotalcite was stirred in 100 ml of aqueous solution of 1.87 mM (0.616 g) sodium tungstate (obtained from M/s. Fluka, a Sigma Aldrich Company, Switzerland), at 293K for 24 h. The solid catalyst was filtered, washed with deionised and decarbonated water and lyophilized to dryness.

b) Preparation of Mg—Al hydrotalcite (LDH) molybdate (Catalyst B):

To reach anion exchange of degree of 12%, 1 g of Mg—Al—Cl hydrotalcite was stirred in 100 ml of aqueous solution of 1.87 mM (0.452 g) sodium molybdate (obtained from M/s. Fluka, a Sigma-Aldrich Company, Switzerland), at 293K for 24 h. The solid catalyst was filtered, washed with deionised and decarbonated water and lyophilized to dryness.

c) Preparation of Mg—Al hydrotalcite (LDH) vanadate (Catalyst C):

To reach anion exchange of degree of 12%, 1 g of Mg—Al—Cl hydrotalcite is stirred in 100 ml of aqueous solution of 1.87 mM (0.456 g) sodium vanadate (obtained from M/s. Fluka, a Sigma-Aldrich Company, Switzerland), at 293K for 24 h. The solid catalyst was filtered, washed with deionised and decarbonated water and lyophilized to dryness.

2. Preparation of Mg—Al hydrotalcite (LDH) nitrate:

Magnesium nitrate hexahydrate (30.8 g, 0.12 mol) and aluminum nitrate nonahydrate (15.0 g, 0.04 mol) were dissolved in 100 ml of deionised and decarbonated water. The pH of the solution was adjusted to 10 by adding 2M NaOH. The resulting suspension was stirred for 2 h at room temperature. The precipitate hydrotalcite was collected by filtration under $N_2$ atmosphere and dried overnight at 80° C.

a) Preparation of Mg—Al hydrotalcite (LDH) tungstate (Catalyst D):

To reach anion exchange of degree of 12%, 1 g of Mg—Al—$NO_3$ hydrotalcite was stirred in 100 ml of aqueous 1.87 mM (0.616 g) sodium tungstate (obtained from M/s. Fluka, a Sigma Aldrich Company, Switzerland), at 293K for 24 h. The solid catalyst was filtered, washed with of deionised and decarbonated water and lyophilized to dryness.

3. Preparation of Mg—Al hydrotalcite (LDH) carbonate:

Mg—Al—$CO_3$ hydrotalcite (3:1) is prepared as follows: An aqueous solution (0.280 l) containing $Mg(NO_3)_2 \cdot 6H_2O$ (0.2808 mol) and $Al(NO_3)_3 \cdot 9H_2O$ (0.093 mol) (obtained from M/s. Fluka, a Sigma Aldrich Company, Switzerland) was added slowly to a second solution (0.280 l) containing NaOH (0.6562 mol) and $Na_2CO_3$ (0.3368 mol) in a 1.0 l round bottomed flask under vigorous stirring. The addition took nearly 3 h. Then the slurry was heated to 338 K for 16 h. The precipitate formed was filtered off and washed with hot distilled water until the pH of the filtrate was 7. The precipitate was dried in an oven at 353 K for 15 h.

a) Preparation of Mg—Al hydrotalcite (LDH) tungstate (Catalyst E):

To reach anion exchange of degree of 12%, 1 g of Mg—Al—$CO_3$ calcined (at 723 K for 6 h in a flow of air)

hydrotalcite was stirred in 100 ml of aqueous solution of 1.87 mM (0.616 g) sodium tungstate (obtained from M/s. Fluka, a Sigma Aldrich Company, Switzerland), at 293K for 24 h. The solid catalyst was filtered, washed with deionised and decarbonated water and lyophilized to dryness.

4. Preparation of Ni—Al hydrotalcite (LDH) chloride:

Ni—Al hydrotalcite chloride (3:1) was prepared as follows: About 200 ml of decarbonated and deionised water was taken into a 1 litre four necked round bottomed flask and stirred at 25° C. with a magnetic stirrer under nitrogen flow. A mixture ($Al^{3+}$=0.05 mol/l), ($Ni^{2+}$=0.15 mol/l) of decarbonated solution of $AlCl_3.9H_2O$ (12.07 g), $NiCl_2.6H_2O$ (35.65 g) (obtained from M/s. Fluka. Sigma Aldrich Company, Switzerland) and aqueous solution of sodium hydroxide (16 g, 0.2 mol/l) were added continuously dropwise from a burette, the pH of the reaction mixture being kept at 10.00–10.2 during the reaction. The precipitate obtained was filtered, washed with deionised and decarbonated water and dried at 70° C. for 15 h.

a) Preparation of Ni—Al hydrotalcite (LDH) tungstate (Catalyst F):

To reach anion exchange of degree of 12%, 1 g of Ni—Al hydrotalcite chloride was stirred in 100 ml of aqueous 1.87 mM (0.616 g) sodium tungstate (obtained from M/s. Fluka, a Sigma Aldrich Company, Switzerland), at room temperature for 24 h. The solid catalyst was filtered, washed with deionised and decarbonated water and lyophilized to dryness.

5. Preparation of Ni—Al hydrotalcite (LDH) nitrate:

Nickel nitrate hexahydrate (34.8 g, 0.12 mol) and aluminum nitrate nonahydrate (15.0 g, 0.04 mol) were dissolved in 100 ml of deionised and decarbonated water. The pH of the solution was adjusted to 10 by adding 2M NaOH. The resulting suspension was stirred for 2 h at room temperature. The precipitate hydrotalcite was collected by filtration under $N_2$ atmosphere and dried overnight at 80° C.

a) Preparation of Ni—Al hydrotalcite (LDH) tungstate (Catalyst G):

To reach anion exchange of degree of 12%, 1 g of Ni—Al—$NO_3$ hydrotalcite was stirred in 100 ml of aqueous 1.87 mM (0.616 g) sodium tungustate (obtained from M/s. Fluka, A Sigma Aldrich Company, Switzerland), at 293K for 24 h. The solid catalyst was filtered, washed with of deionised and decarbonated water and lyophilized to dryness.

6. Preparation of $Bu_4N)_3PO_4[WO(O_2)_2]_4$:

Hydrogen peroxide (30% w/w) 100 mmol (10 ml) was added to a solution of $H_3[PW_{12}O_{40}]$ 6 mmol of tungsten (or 1.65 g) in 1 ml of water. After 30 min an aqueous solution of tetrabutylammonium chloride (1.6 mmol) was slowly added. The resulting white precipitate was filtered out and washed with several times with water than air-dried.

a) Preparation of LDH-$\{[PO_4WO(O_2)]_4\}$(Catalyst H):

The above synthesized complex (0.46 mmol) was exchanged on 1.0 g of Mg—Al—Cl LDH in 3 ml of water, to this 1 ml of hydrogen peroxide (30%, w/w) was added drop-wise and stirring was continued for 16 h at room temperature. Finally the catalyst was filtered and washed with water and water-acetone (1:1), acetone and dried on vacuum.

EXAMPLE 2

Oxidation of N-methylmorpholine catalysed by tungstate exchanged with Mg/Al (3:1) layered double hydroxides using aqueous hydrogen peroxide The four-necked flask was charged with 0.22 ml (2 mmol) of N-methylmorpholine, 200 mg of catalyst A and 50 ml of water. To the mixture was added dropwise 6.6 ml (6 mmol) of a 30% by weight of aqueous solution of hydrogen peroxide for period of 0.5 hours in 2 to 3 portions at 25° C. under continuous stirring. Continued the reaction for another 0.5 hour. After the completion of the reaction (followed by TLC), the catalyst was filtered off and washed with methanol. To the filtrate a small amount of manganese dioxide was added to decompose the unreacted hydrogen peroxide. The treated reaction mixture was filtered to remove the solid $MnO_2$ and concentrated under reduced pressure to obtain the product. The product thus obtained was purified by column chromatography to afford the corresponding amine oxide. N-methylmorpholine N-oxide of 96% yield was obtained. This product is commercially available from Fluka, Aldrich, Lancaster and Merck companies.

EXAMPLE 3

Oxidation of N-methylmorpholine catalysed by tungstate exchanged with Mg/Al (3:1) layered double hydroxides using aqueous hydrogen peroxide: recycle-I The oxidation reaction of N-methylmorpholine by using catalyst A which had been used in example 2 was performed in an identical procedure as detailed in example 2, without further addition of fresh catalyst. N-methylmorpholine N-oxide of 96% yield was obtained.

EXAMPLE 4

Oxidation of N-methylmorpholine catalysed by tungstate exchanged with Mg/Al (3:1) layered double hydroxides using aqueous hydrogen peroxide: recycle-II The oxidation reaction of N-methylmorpholine by using catalyst A which had been used in example 3 was performed in an identical procedure as detailed in example 2, without further addition of fresh catalyst. N-methylmorpholine N-oxide of 95% yield was obtained.

EXAMPLE 5

Oxidation of N-methylmorpholine catalysed by tungstate exchanged with Mg/Al (3:1) layered double hydroxides using aqueous hydrogen peroxide: recycle-III The oxidation reaction of N-methylmorpholine by using catalyst A which had been used in example 4 was performed in an identical procedure as detailed in example 2, without further addition of fresh catalyst. N-methylmorpholine N-oxide of 94% yield was obtained.

EXAMPLE 6

Oxidation of N-methylmorpholine catalysed by tungstate exchanged with Mg/Al (3:1) layered double hydroxides using aqueous hydrogen peroxide: recycle-IV The oxidation reaction of N-methylmorpholine by using catalyst A which had been used in example 5 was performed in an identical procedure as detailed in example 2, without further addition of fresh catalyst. N-methylmorpholine N-oxide of 94% yield was obtained.

EXAMPLE 7

Oxidation of N-methylmorpholine catalysed by tungstate exchanged with Mg/Al (3:1) layered double hydroxides using aqueous hydrogen peroxide: recycle-V The oxidation reaction of N-methylmorpholine by using catalyst A which had been used in reaction 6 in an identical procedure as detailed in example 2, without further addition of fresh catalyst. N-methylmorpholine N-oxide of 95% yield was obtained.

EXAMPLE 8

Oxidation of N-methylmorpholine catalysed by molybdate exchanged with Mg/Al (3:1) layered double hydroxides using aqueous hydrogen peroxide The oxidation reaction of N-methylmorpholine was performed using catalyst B in an identical procedure as detailed in Example 2. The time taken for the completion of reaction was 3.5 hours. N-methylmorpholine N-oxide of 90% yield was obtained.

EXAMPLE 9
Oxidation of N-methylmorpholine catalysed by vanadate exchanged with Mg/Al (3:1) layered double hydroxides using aqueous hydrogen peroxide The oxidation reaction of N-methylmorpholine was performed using Catalyst C in an identical procedure as detailed in Example 2. The time taken for the completion of reaction was 3.5 hours. N-methylmorpholine N-oxide of 40% yield was obtained.

EXAMPLE 10
Oxidation of N-methylmorpholine catalysed by tungstate exchanged with Mg/Al (3:1) layered double hydroxides using aqueous hydrogen peroxide The oxidation reaction of N-methylmorpholine was performed using catalyst D in an identical procedure as detailed in Example 2. N-methylmorpholine N-oxide of 95% yield was obtained.

EXAMPLE 11
Oxidation of N-methylmorpholine catalysed by tungstate exchanged with Mg/Al (3:1) layered double hydroxides using aqueous, hydrogen peroxide The oxidation reaction of N-methylmorpholine was performed using catalyst E in an identical procedure as detailed in Example 2. N-methylmorpholine N-oxide of 96% yield was obtained.

EXAMPLE 12
Oxidation of N-methylmorpholine catalysed by tungstate exchanged with Mg/Al (3:1) layered double hydroxides using aqueous hydrogen peroxide The oxidation reaction of N-methylmorpholine was performed using catalyst F in an identical procedure as detailed in Example 2. The time taken for the completion of reaction was 1.5 hours. N-methylmorpholine N-oxide of 95% yield was obtained.

EXAMPLE 13
Oxidation of N-methylmorpholine catalysed by tungstate exchanged with Mg/Al (3:1) layered double hydroxides using aqueous hydrogen peroxide The oxidation reaction of N-methylmorpholine was performed using catalyst G in an identical procedure as detailed in Example 2. The time taken for the completion of reaction was 1.5 hours. N-methylmorpholine N-oxide of 95% yield was obtained.

EXAMPLE 14
Oxidation of N-methylmorpholine catalysed by LDH-$\{[PO_4WO(O_2)]_4\}$:

The oxidation reaction of N-methylmorpholine was performed using catalyst H in an identical procedure as detailed in Example 2. The time taken for the completion of reaction was 3.5 hours. N-methylmorpholine N-oxide of 40% yield was obtained.

EXAMPLE 15
Oxidation of N-methylmorpholine catalysed by $Na_2WO_4$

The oxidation reaction of N-methylmorpholine was performed using $Na_2WO_4$ in an identical procedure as detailed in Example 2. The time taken for the completion of reaction was 3.5 hours. N-methylmorpholine N-oxide of 75% yield was obtained.

EXAMPLE 16
Oxidation of N-methylmorpholine catalysed by $Na_2VO_3$

The oxidation reaction of N-methylmorpholine was performed using $Na_2VO_3$ in an identical procedure as detailed in Example 2. The time taken for the completion of reaction was 3.5 hours. N-methylmorpholine N-oxide of 15% yield was obtained.

EXAMPLE 17
Oxidation of N-methylmorpholine catalysed by $Na_2MoO_4$

The oxidation reaction of N-methylmorpholine was performed using $Na_2MoO_4$ in an identical procedure as detailed in Example 2. The time taken for the completion of reaction was 3.5 hours. N-methylmorpholine N-oxide of 48% yield was obtained.

EXAMPLE 18
Oxidation of N-methylmorpholine catalysed by tungstate exchanged with Mg/Al (3:1) layered double hydroxides using aqueous hydrogen peroxide The four-necked flask was charged with 0.22 ml (2 mmol) of N-methylmorpholine, 200 mg of catalyst A and 50 ml of water. To this 6 mg of dodecylbenzenesulfonic acid sodium salt was added as surfactant was added as surfactant. To the mixture was added dropwise 6.6 ml (6 mmol) of a 30% by weight of aqueous solution of hydrogen peroxide for period of 0.5 hours in 2 to 3 portions at 25° C. under continuous stirring. Continued the reaction for another 0.5 hour. After the completion of the reaction (followed by TLC), the catalyst was filtered off and washed with methanol. To the filtrate a small amount of manganese dioxide was added to decompose the unreacted hydrogen peroxide. The treated reaction mixture was filtered to remove the solid $MnO_2$ and concentrated under reduced pressure to obtain the product. The product thus obtained was purified by column chromatography to afford the corresponding amine oxide. N-methylmorpholine N-oxide of 96% yield was obtained. This product is commercially available from Fluka, Aldrich, Lancaster and Merck companies.

EXAMPLE 19
Oxidation of triethyl amine catalysed by tungstate exchanged with Mg/Al (3:1) layered double hydroxides using aqueous hydrogen peroxide The oxidation reaction of triethyl amine by using catalyst A was performed in an identical procedure as detailed in example 2. The time taken for the completion of reaction was 3 hours. Triethyl amine N-oxide of 96% yield was obtained.

EXAMPLE 20
Oxidation of triethyl amine catalysed by tungstate exchanged with Mg/Al (3:1) layered double hydroxides using aqueous hydrogen peroxide The oxidation reaction of triethyl amine by using catalyst A was performed in an identical procedure as detailed in example 18. The time taken for the completion of reaction was 1.5 hours. Triethyl amine N-oxide of 96% yield was obtained.

EXAMPLE 21
Oxidation of tributyl amine catalysed by tungstate exchanged with Mg/Al (3:1) layered double hydroxides using aqueous hydrogen peroxide The oxidation reaction of tributyl amine was performed by using catalyst A in an identical procedure as detailed in example 2. The time taken for the completion of reaction was 3 hours. Tributyl amine N-Oxide of 94% yield was obtained.

EXAMPLE 22
Oxidation of N,N-dibutyl benzylamine catalysed by tungstate exchanged with Mg/Al (3:1) layered double hydroxides using aqueous hydrogen peroxide The oxidation reaction of N,N-dibutyl benzylamine was performed by using catalyst A in an identical procedure as detailed in example 2. The time taken for the completion of reaction was 1.5 hours. N,N-dibutyl benzyl amine N-oxide of 96% yield was obtained.

EXAMPLE 23
Oxidation of N,N-dibutyl benzylamine catalysed by tungstate exchanged with Mg/Al (3:1) layered double hydroxides using aqueous hydrogen peroxide The oxidation reaction of N,N-dibutyl benzylamine was performed by using catalyst A in an identical procedure as detailed in example 18. N,N-dibutyl benzyl amine N-oxide of 95% yield was obtained.

EXAMPLE 24
Oxidation of N-benzyl piperidine catalysed by tungstate exchanged with Mg/Al (3:1) layered double hydroxides using aqueous hydrogen peroxide The oxidation reaction of N-benzyl piperidine was performed by using catalyst A, in an identical procedure as detailed in example 2. The time taken for the completion of reaction was 3 hours. N-benzyl piperidine N-oxide of 97% yield was obtained.

EXAMPLE 25
Oxidation of N-benzyl piperidine catalysed by tungstate exchanged with Mg/Al (3:1) layered double hydroxides using aqueous hydrogen peroxide The oxidation reaction of N-benzyl piperidine was performed by using catalyst A, in an identical procedure as detailed in example 18. N-benzyl piperidine N-oxide of 97% yield was obtained.

EXAMPLE 26
Oxidation of N,N-dimethyldecylamine catalysed by tungstate exchanged with Mg/Al (3:1) layered double hydroxides using aqueous hydrogen peroxide The oxidation reaction of N,N-dimethyldecylamine was performed by using catalyst A in an identical procedure as detailed in example 2. The time taken for the completion of reaction was 2.5 hours. N,N-dimethyldecylamine N-oxide of 97% yield was obtained. This product is commercially available from Lonza Inc. With trade name Barlox 10S (Specification: 30 weight percent decyldimethyl tertiary amine oxide).

EXAMPLE 27
Oxidation of N,N-dimethyloctylamine catalysed by tungstate exchanged with Mg/Al (3:1) layered double hydroxides using aqueous hydrogen peroxide The oxidation reaction of N,N-dimethyloctylamine was performed by using catalyst A in an identical procedure as detailed in example 2. The time taken for the completion of reaction was 2.5 hours. N,N-dimethyloctylamine N-oxide of 95% yield was obtained.

EXAMPLE 28
Oxidation of N,N-dimethyloctylamine catalysed by tungstate exchanged with Mg/Al (3:1) layered double hydroxides using aqueous hydrogen peroxide The oxidation reaction of N,N-dimethyloctylamine was performed by using catalyst A in an identical procedure as detailed in example 18. N,N-dimethyloctylamine N-oxide of 95% yield was obtained.

EXAMPLE 29
Oxidation of N,N-dimethyl benzylamine catalysed by tungstate exchanged with Mg/Al (3:1) layered double hydroxides using aqueous hydrogen peroxide The oxidation reaction of N,N-dimethyl benzylamine was performed by using catalyst A in an identical procedure as in Example 2. The time taken for the completion of reaction was 1.5 hours. N,N-dimethyl benzylamine amine N-oxide of 95% yield was obtained.

EXAMPLE 30
Oxidation of N,N-dimethyl benzylamine catalysed by tungstate exchanged with Mg/Al (3:1) layered double hydroxides using aqueous hydrogen peroxide The oxidation reaction of N,N-dimethyl benzylamine was performed by using catalyst A in an identical procedure as in example 18. N,N-dimethyl benzylamine amine N-oxide of 96% yield was obtained.

EXAMPLE 31
Oxidation of N,N-dimethylcyclohexylamine catalysed by tungstate exchanged with Mg/Al (3:1) layered double hydroxides using aqueous hydrogen peroxide The oxidation reaction of N,N-dimethylcyclohexylamine by using catalyst A was performed in an identical procedure as detailed in example 2. The time taken for the completion of reaction was 3 hours. N,N-dimethylcyclohexylamine N-oxide of 96% yield was obtained.

EXAMPLE 32
Oxidation of N,N-dimethylcyclohexylamine catalysed by tungstate exchanged with Mg/Al (3:1) layered double hydroxides using aqueous hydrogen peroxide The oxidation reaction of N,N-dimethylcyclohexylamine by using catalyst A was performed in an identical procedure as detailed in example 18. N,N-dimethylcyclohexylamine N-oxide of 95% yield was obtained.

EXAMPLE 33
Oxidation of dibutyl amine catalysed by tungstate exchanged with Mg/Al (3:1) layered double hydroxides using aqueous hydrogen peroxide The oxidation reaction of dibutyl amine was performed by using catalyst D in an identical procedure as detailed in example 2. The time taken for the completion of reaction was 3 hours. N-butylidene-butylamine N-oxide of 96% yield was obtained.

EXAMPLE 34
Oxidation of dibutyl amine catalysed by tungstate exchanged with Mg/Al (3:1) layered double hydroxides using aqueous hydrogen peroxide The oxidation reaction of dibutyl amine was performed by using catalyst E in an identical procedure as detailed in example 2. The time taken for the completion of reaction was 3 hours. N-butylidene-butylamine N-oxide of 95% yield was obtained.

EXAMPLE 35
Oxidation of dibutyl amine catalysed by tungstate exchanged with Ni/Al (3:1) layered double hydroxides using aqueous hydrogen peroxide The oxidation reaction of dibutyl amine was performed by using catalyst F in an identical procedure as detailed in example 2. The time taken for the completion of reaction was 3 hours. N-butylidene-butylamine N-oxide of 96% yield was obtained.

EXAMPLE 36
Oxidation of dibutyl amine catalysed by tungstate exchanged with Ni/Al (3:1) layered double hydroxides using aqueous hydrogen peroxide The oxidation reaction of dibutyl amine was performed by using catalyst G in an identical procedure as detailed in example 2. The time taken for the completion of reaction was 3 hours. N-butylidene-butylamine N-oxide of 95% yield was obtained.

EXAMPLE 37
Oxidation of dibutyl amine catalysed by tungstate exchanged with Mg/Al (3:1) layered double hydroxides using aqueous hydrogen peroxide The oxidation reaction of dibutyl amine was performed by using catalyst A in an identical procedure as detailed in example 2. The time taken for the completion of reaction was 3 hours. N-butylidene-butylamine N-oxide of 97% yield was obtained.

EXAMPLE 38
Oxidation of dibenzyl amine catalysed by tungstate exchanged with Mg/Al (3:1) layered double hydroxides using aqueous hydrogen peroxide The oxidation reaction of dibenzyl amine was performed by using of catalyst A in an identical procedure as detailed in example 2. The time taken for the completion of reaction was 5 hours. N-benzylidenebenzylamine N-oxide of 60% yield was obtained.

EXAMPLE 39
Oxidation of N-benzyl phenethylamine catalysed by tungstate exchanged with Mg/Al (3:1) layered double hydroxides using aqueous hydrogen peroxide The oxidation reaction of N-benzyl phenethylamine was performed by using catalyst A in an identical procedure as in example 2. The time taken for the completion of reaction was 6 hours. N-(1-methyl benzylidine) phenylamine N-oxide of 90% yield was obtained.

EXAMPLE 40
Oxidation of N-phenyl benzylamine amine catalysed by tungstate exchanged with Mg/Al (3:1) layered double hydroxides using aqueous hydrogen peroxide The reaction oxidation reaction of N-phenyl benzylamine was performed by using catalyst A in an identical procedure as detailed in example 2. The time taken for the completion of reaction was 4 hours. N-bezylidine phenylamine N-oxide of 93% yield was obtained.

EXAMPLE 41
Oxidation piperidine catalysed by tungstate exchanged with Mg/Al (3:1) layered double hydroxides using aqueous hydrogen peroxide The oxidation reaction of piperidine by using catalyst A was performed in an identical procedure as detailed in example 2. The time taken for completion of reaction was 3 hours. 2,3,4,5 tetrahydro pyridine N-oxide of 92% yield was obtained.

EXAMPLE 42
Oxidation of 1,2,3,4-tetrahydroisoquinoline catalysed by tungstate exchanged with Mg/Al (3:1) layered double hydroxides using aqueous hydrogen peroxide The oxidation reaction of 1,2,3,4-tetrahydroisoquinoline performed by using catalyst A in an identical procedure as detailed in example 2. The time taken for completion of reaction was 5 hours. 3,4 dihydroisoquinoline N-oxide of 93% yield was obtained.

EXAMPLE 43
Oxidation of diisopropyl amine catalysed by tungstate exchanged with Mg/Al (3:1) layered double hydroxides using aqueous hydrogen peroxide The reaction oxidation reaction of diisopropyl amine was performed by using catalyst A in an identical procedure as detailed in example 2. The time taken for the completion of reaction was 3 hours. N-(1-methylethylidine)-1-methylethylamine N-oxide of 92% yield was obtained.

TABLE 1

Reusability of the catalyst in the oxidation of N-methylmorpholine catalysed by tungstate exchanged with Mg/Al (3:1) layered double hydroxides (Catalyst A) using aqueous hydrogen peroxide[a]

| Ex. No | Tertiary amine | Cycle | Time(h) | Amine oxide | Yield[b] |
|---|---|---|---|---|---|
| 2 | N-methyl-morpholine | 1 | 1.0 | N-methylmorpholine N-oxide | 96 |
| 3 | N-methyl-morpholine | 2 | 1.0 | N-methylmorpholine N-oxide | 95 |
| 4 | N-methyl-morpholine | 3 | 1.0 | N-methylmorpholine N-oxide | 94 |
| 5 | N-methyl-morpholine | 4 | 1.0 | N-methylmorpholine N-oxide | 94 |
| 6 | N-methyl-morpholine | 5 | 1.0 | N-methylmorpholine N-oxide | 94 |
| 7 | N-methyl-morpholine | 6 | 1.0 | N-methylmorpholine N-oxide | 95 |

[a]Reaction conditions as exemplified in example 2
[b]Isolated yields

TABLE 2

The catalytic N-oxidation of N-methylmorpholine to N-methylmorpholine N-oxide in water using various metal ion-exchanged LDH catalysts and their homogeneous analogues[a]

| Ex. No. | Catalyst | Time(h) | Yield[b] |
|---|---|---|---|
| 8 | LDH-$MoO_4^{2-}$ (Catalyst B) | 3.5 | 90 |
| 9 | LDH-$VO_3^-$ (Catalyst C) | 3.5 | 40 |
| 10 | LDH-$WO_4^{2-}$ (Catalyst D) | 1.0 | 95 |
| 11 | LDH-$WO_4^{2-}$ (Catalyst E) | 1.0 | 96 |
| 12 | Ni—Al-LDH-$WO_4^{2-}$ (Catalyst F) | 1.5 | 95 |
| 13 | Ni—Al-LDH-$WO_4^{2-}$ (Catalyst G) | 1.5 | 96 |
| 14 | LDH-$\{PO_4WO(O_2)]_4\}$ (Catalyst H) | 3.5 | 40 |
| 15 | $Na_2WO_4$ | 3.5 | 75 |
| 16 | $NaVO_3$ | 3.5 | 15 |
| 17 | $Na_2MoO_4$ | 3.5 | 48 |

[a]Reaction conditions as exemplified in example 2
[b]Isolated yields

TABLE 3

N-oxidation of aliphatic tert-amines catalysed by LDH-$WO_4^{2-}$ (Catalyst A) in water[a] (procedure I) or water in combination of dodecylbenzenesufonic acid sodium salt[b] (procedure II).

| Ex. No | Tertiary amine | Procedure | Amine oxide | Time(h) | Yield[c] |
|---|---|---|---|---|---|
| 18 | N-methyl morpholine | II | N-methylmorpholine N-oxide | 1.0 | 96 |

TABLE 3-continued

N-oxidation of aliphatic tert-amines catalysed by LDH-WO$_4^{2-}$ (Catalyst A) in water[a] (procedure I) or water in combination of dodecylbenzenesufonic acid sodium salt[b] (procedure II).

| Ex. No | Tertiary amine | Procedure | Amine oxide | Time(h) | Yield[c] |
|---|---|---|---|---|---|
| 19 | Triethyl amine | I | Triethyl amine N-oxide | 3.0 | 96 |
| 20 | Triethyl amine | II | Triethyl amine N-oxide | 1.5 | 96 |
| 21 | Tributyl amine | I | Tributyl amine N-oxide | 3.0 | 94 |
| 22 | N,N-dibutyl benzyl amine | I | N,N-dibutyl benzyl amine N-oxide | 1.5 | 96 |
| 23 | N,N-dibutyl benzyl amine | II | N,N-dibutyl benzyl amine N-oxide | 1.0 | 95 |
| 24 | N-benzyl piperidine | I | N-benzyl piperidine N-oxide | 3.0 | 97 |
| 25 | N-benzyl piperidine | II | N-benzyl piperidine N-oxide | 1.0 | 97 |
| 26 | N,N-dimethyl decyl amine | I | N,N-dimethyl decyl amine N-oxide | 2.5 | 97 |
| 27 | N,N-dimethyl octyl amine | I | N,N-dimethyl octyl amine N-oxide | 2.5 | 95 |
| 28 | N,N-dimethyl octyl amine | II | N,N-dimethyl octyl amine N-oxide | 1.0 | 95 |
| 29 | N,N-dimethyl benzyl amine | I | N,N-dimethyl benzyl amine N-oxide | 1.5 | 95 |
| 30 | N,N-dimethyl benzyl amine | II | N,N-dimethyl benzyl amine N-oxide | 1.0 | 96 |
| 31 | N,N-dimethyl cyclohexylamine | I | N,N-dimethyl yclohexylamine N-oxide | 3.0 | 96 |
| 32 | N,N-dimethyl cyclohexylamine | II | N,N-dimethyl yclohexylamine N-oxide | 1.0 | 95 |

[a]Reaction conditions as exemplified in example 2
[b]Reaction conditions as exemplified in example 18
[b]Isolated yields

TABLE 4

Oxidation of secondary amines catalysed by anion of transition metal oxides exchanged layered double hydroxides using aqueous hydrogen peroxide[a]

| Ex. No | Secondary amine | Catalyst | Amine oxide (nitrone) | Time(h) | Yield[b] |
|---|---|---|---|---|---|
| 33 | Dibutyl amine | D | N-butylidene-butylamine N-oxide | 3 | 96 |
| 34 | Dibutyl amine | E | N-butylidene-butylamine N-oxide | 3 | 95 |
| 35 | Dibutyl amine | F | N-butylidene-butylamine N-oxide | 3 | 96 |
| 36 | Dibutyl amine | G | N-butylidene-butylamine N-oxide | 3 | 95 |
| 37 | Dibutyl amine | A | N-butylidene-butylamine N-oxide | 3 | 97 |
| 38 | Dibenzyl amine | A | N-benzylidene benzylamine N-oxide | 5 | 60 |
| 39 | N-benzyl phenethyl amine | A | N-(1-methylbenzylidene) benzylamine N-oxide | 6 | 90 |
| 40 | N-Phenyl benzyl amine | A | N-benzylidene phenylamine N-oxide | 4 | 93 |
| 41 | Piperidine | A | 2,3,4,5 Tetrahydro pyridine N-oxide | 3 | 92 |
| 42 | 1,2,3,4 Tetrahydro isoquinoline | A | 3,4, Dihydroisoquinoline N-oxide | 5 | 93 |
| 43 | Diisopropyl amine | A | N-(1-ethylethylidene(1-methylethylamine N-oxide | 3 | 92 |

[a]Reaction conditions as exemplified in example 2
[b]Isolated yields

The main advantages of the present invention are:
1. The present process is eco-friendly and simple.
2. The catalyst is cheap, non-corrosive, recyclable for several times and heterogeneous in nature.
3. The reactions are conducted in water, an eco-friendly benign solvent.
4. The reaction conditions are very mild, being the reaction temperature ranges between 10–25° C.

5. The hydrogen peroxide used is 30% by weight, which is more environmentally friendly.

6. The process is economical and is accomplished in short time with high productivity.

7. The amount of effluents formed in this process is minimized because the catalyst and solvent are recovered/recycled and reused.

8. The process provides high quality of the product without resulting in gel formation, during the course of reaction.

We claim:

1. A process for the preparation of high quality amine oxide which comprises reacting a tertiary or secondary amine with hydrogen peroxide as an oxidant in presence of a recyclable heterogeneous layered double hydroxide exchanged with one of the anions of transition metal oxides as a catalyst in a solvent selected from the group consisting of water, water containing dodecylbenzenesulfonic acid sodium salt as additive, and a water miscible organic solvent at a temperature ranging between 10–25° C. for a period of 1–6 hours under continuous stirring and separating the product by simple filtration and subsequently evaporation of solvents.

2. A process as claimed in claim 1 wherein the heterogeneous catalyst used is layered double hydroxide with transition metal oxides selected from a group consisting of tungstate, molybdate, vanadate and their polyanions as polyoxometalates having formula I: $[M^{II}_{(1-x)}M^{III}_{x}(OH)_2][M^{n-1}_{x/2}.zH_2O$ which is derived from LDH having formula II$[M^{II}_{(1-x)}M^{III}_{x}(OH)_2][A^{n-1}_{x/2}, zH_2O$ where M is an anion of transition metal oxide selected from a group consisting of W, Mo, V and $A^{n-}$ is an interstitial anion, selected from nitrate, chloride and $M^{II}$ is a divalent cation selected from the group consisting of $Mg^{2+}$, $Mn^{2+}$, $Fe^{2+}$, $V^{2+}$, $Co^{2+}$, $Ni^{2+}$, $Cu^{2+}$, $Zn^{2+}$ $Pd^{2+}$, or $Ca^{2+}$ and $M^{III}$ is a trivalent ion selected from the group consisting of $Al^{3+}$, $Cr^{3+}$, $V^{3+}$, $Mn^{3+}$, $Fe^{3+}$, $Co^{3+}$, $Ni^{3+}$, $Rh^{3+}$, $Ru^{3+}$, $Ga^{3+}$ or $La^{3+}$, x is the mole fraction having integral value ranging from 0.2 to 0.33 and z is the number of water molecules and ranges from 1 to 4.

3. A process as claimed in claim 1 wherein the tertiary amines, having the general formula $R^1R^2NR^3$ wherein $R^1$, $R^2$ and $R^3$ are the same or different and are straight-chain or branched-chain groups selected from alkyl, alkenyl and aralkyls having $C_1$–$C_{24}$ carbons selected from dimethyl decyl amine, dimethyl docyl amine, dimethylbenzylamine, cyclic amines from imidazolines pyridines, N-substituted piperazines, or N-substituted morpholines.

4. A process as claimed in claim 1 wherein in the secondary amines used in the system have the general formula $R^1R^2NH$ wherein $R^1$ and $R^2$ may be the same or different and are the straight-chain or branched chain groups selected from alkyl, alkenyl and aralkyls having $C_1$–$C_{24}$ carbons selected from dibutyl amine, dibenzyl amine, N-benzyl phenethylamine, N-phenyl benzylamine, cyclic amines selected from piperidine, 1,2,3,4 tetrahydro iso-quinoline.

5. A process as claimed in claim 1 wherein 30% by weight of aqueous hydrogen peroxide is added slowly in a controlled manner during the period specified.

6. A process as claimed in claim 1 wherein the catalyst introduced in the system is 6–12 weight % anion of transition metal oxides selected from tungstate, molybdate, vanadate and their polyanions as polyoxometalates.

7. A process as claimed in claim 1 wherein the water miscible organic solvents used for the reaction are selected from the group consisting of methanol, ethanol, 1-propanol, 2-propanol, 1-butanol, 2-butanol and isobutyl alcohol.

8. A process as claimed in claim 1 wherein the amount of hydrogen peroxide used ranges between 2 to 6 moles per mole of secondary or tertiary amine.

\* \* \* \* \*